United States Patent [19]

Purdum

[11] Patent Number: 4,483,705

[45] Date of Patent: Nov. 20, 1984

[54] ALKYLPHOSPHONATE DIESTERS AND MONOESTERS OF N-PHOSPHONOMETHYLGLYCINATE AS HERBICIDES

[75] Inventor: William R. Purdum, Maryland Heights, Mo.

[73] Assignee: Monsanto Co., St. Louis, Mo.

[21] Appl. No.: 479,247

[22] Filed: Mar. 28, 1983

Related U.S. Application Data

[63] Continuation-in-part of Ser. No. 275,461, Jun. 19, 1981, abandoned.

[51] Int. Cl.³ .................... A01N 57/20; A01N 57/24; C07F 9/40
[52] U.S. Cl. .................................. 71/086; 260/941; 548/112; 549/218; 549/221
[58] Field of Search .................. 260/941; 548/112; 549/218, 221; 71/86

[56] References Cited

U.S. PATENT DOCUMENTS 4,388,102 6/1983 Purdum .................. 260/941

Primary Examiner—Anton H. Sutto
Attorney, Agent, or Firm—David Bennett; Arnold H. Cole; Richard H. Shear

[57] ABSTRACT

Alkylphosphonate diesters and monoesters of N-phosphonomethylglycine are disclosed which are useful as herbicides. This invention further relates to herbicidal compositions containing such alkylphosphonate diesters and monoesters of N-phosphonomethylglycine and to herbicidal methods employing such compounds and compositions.

25 Claims, No Drawings

ALKYLPHOSPHONATE DIESTERS AND MONOESTERS OF N-PHOSPHONOMETHYLGLYCINATE AS HERBICIDES

This is a continuation in part of U.S. application Ser. No. 275,461, filed June 19, 1981 now abandoned.

This invention relates to mono and diesters of N-phosphonomethylglycinate which are useful as herbicides. More particularly this invention relates to alkyl phosphonate mono and diesters of N-phosphonomethylglycinate which are useful as herbicides and to herbicidal methods employing such compounds and compositions.

U.S. Pat. No. 4,025,331 issued to Jean-Pierre Leber on May 24, 1977 discloses N-phosphonomethylglycine derivatives of the formula

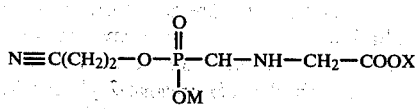

wherein X is hydrogen, unsubstituted or substituted hydrocarbon or a cation and M is hydrogen or a cation. The compounds disclosed in U.S. Pat. No. 4,025,331 supra are said to possess herbicidal and plant growth regulating properties.

The compounds of the present invention are represented by the formula

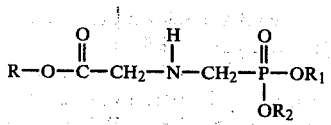

wherein R is lower alkyl; $R_1$ is a

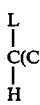

group wherein n is an integer of from 0 to 4, L is hydrogen or lower alkyl and Y is selected from the group consisting of trihalomethyl, alkoxycarbonyl, furanyl, pyrrolidinyl, pyranyl group and a

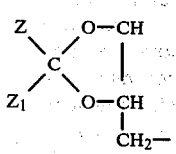

group wherein Z and $Z_1$ are independently lower alkyl, and $R_2$ is hydrogen or a group represented by $R_1$.

As employed throughout the claims and description, the term "lower alkyl" includes alkyl radicals which have up to four carbon atoms in a straight or branched chain, for example, methyl, ethyl, propyl, isopropyl, butyl, isobutyl, sec-butyl and t-butyl.

In accordance with the present invention alkylphosphonate diesters of N-phosphonomethylglycinate of the formula

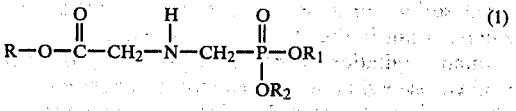

may be prepared by simultaneously reacting a trialkylphosphite of the formula

wherein $R_1$ is defined as recited above with water and with 1,3,5-tri-(alkoxycarbonylmethyl) hexahydro-1,3,5-triazine (trimer of the Schiff's base of formaldehyde and a corresponding lower alkyl glycinate) of the formula

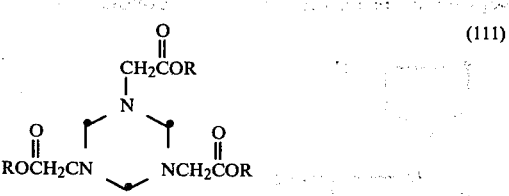

wherein R is as aforedefined to form a crude diester composition containing diester product. A purified diester product may be recovered from the crude diester composition by employing distillation means as, for example, employing a chromatographic or distillation means having sufficient capability and capacity to effect the aforedescribed recovery.

The triester component of the reaction mixture can be obtained by reacting phophorous trichloride with three equivalents of the corresponding alcohol ($R_1$OH) in the presence of a base such as triethylamine in a suitable solvent. Such a process is described in "Organic Phosphorous Compounds" (Vol. 5) by G. M. Kosolapoff and L. Maier (Wiley-Interscience, 1973) at pp. 32–37.

The triazine components used in the above-described process are well known condensation products of formaldehyde with an amine. Triazines of the type useful in the present invention are described for example, in "S-Triazines and Derivatives" by E. M. Smolin and L. Rapoport, (Interscience 1959), pp. 480–3.

The aforedescribed reaction is carried out at a temperature in the range from about 10° to 110° and preferably from about 20° to about 100° C.

In preparing diester compounds of formula (1), the range of reactants is not narrowly critical. Preferably, however for each mole of trialkylphosphite employed, one should employ from about 0.5 to about 1.5 mole water, about ¼ to about ½ mole 1,3,5-tri-1(alkoxycarbonylmethyl)hexahydro-1,3,5-triazine.

While no catalyst is required for the aforedescribed reaction to proceed a catalyst may be employed if desired.

The reaction time is in the range from about 1 to about 72 and is preferably from about 2 to about 50 hours.

While the process of this invention can be conducted at atmospheric, sub-atmospheric or super-atmospheric pressure, for convenience and economy it is generally preferred to conduct these processes at atmospheric pressure.

Although a suitable solvent may be employed in the aforedescribed process, it is preferred that the reaction be carried out in the absence of a solvent.

Suitable agitation is provided, preferably by stirring or otherwise agitating the reaction composition.

In practicing the aforedescribed process the aforedescribed reactants are admixed together in any desired order to form the reaction composition.

The following Examples are presented to define the invention more completely without any intention of being limited thereby. All parts and percentages are by weight, unless otherwise specified.

As indicated above the triphosphite esters are obtained by the reaction of phosphorous trichloride with the appropriate alcohol in the presence of a base. The triphosphite esters employed in the following Examples are prepared using the following alcohols:

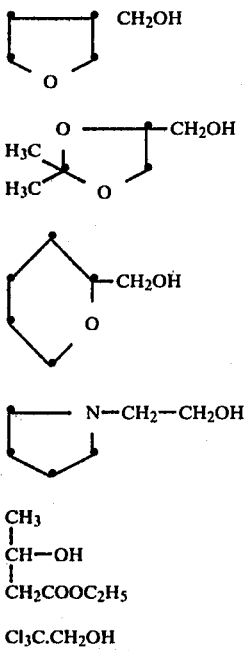

EXAMPLE 1

A reaction composition comprising 15.0 g (0.045 mole) tri-(2-furanylmethyl)phosphite, 0.81 g (0.045 mole) water, and 5.18 g (0.015 mole) 1,3,5-tri(ethoxycarbonylmethyl)hexahydro-1,3,5-triazine was heated at about 100° to about 110° C. for a time of 3 hours. An alcohol, 2-furanylmethanol coproduct was removed by employing bulb to bulb distillation of the reaction mixture at 75° C. and 0.05 mm Hg. The distillation residue was chromatographed on silica gel with an eluent of ethyl acetate. The product, glycine, N-[[bis(2-furanylmethoxy)phosphinyl]methyl]-, ethyl ester was obtained as a viscous yellow oil in 36.6% yield (6.0 g) having the following analysis:

Calc'd: C, 49.31; H, 7.72; N, 3.83; P, 8.48; Found: C, 49.45; H, 8.33; N, 3.38; P, 7.56.

EXAMPLE 2

A reaction composition comprising 15.0 g (0.0353 mole) tri-[(2,2-dimethyl-1,3-dioxolan-4-yl)methyl]phosphite, 0.64 g (0.0353 mole) water, and 4.07 g (0.0118 mole) 1,3,5-tri(ethoxycarbonylmethyl)hexahydro-1,3,5-triazine was heated at about 100° to about 110° C. for a time of 4 hours. An alcohol 2,2-dimethyl-1,3-dioxolan-4-yl methanol coproduct was removed by employing bulb to bulb distillation of the reaction mixture at 80° C. and 0.1 mm Hg. The distillation residue was chromatographed on silica gel with an eluent of ethyl acetate. The product, glycine, N-[[bis[(2,2-dimethyl-1,3-dioxolan-4-yl)methoxy]phosphinyl]methyl]-, ethyl ester was obtained as a viscous yellow oil in 35% yield (5.2 g) having the following analysis:

Calculated: C, 48.00; H, 7.58; N, 3.29; P, 7.28; Found: C, 48.57; H, 7.60; N, 2.74; P, 6.73.

EXAMPLE 3

A reaction composition comprising 15.0 g (0.04 mole) tri-[(tetrahydro-2H-pyran-2-yl)methyl]phosphite, 0.72 g (0.04 mole) water, and 4.6 g (0.0133 mole) 1,3,5-tri(ethoxycarbonylmethyl)hexahydro-1,3,5-triazine was heated at about 100° to about 110° C. for a time of 3 hours. An alcohol (tetrahydro-2H-pyran-2-yl) methanol coproduct was removed by employing bulb to bulb distillation of the reaction mixture at 75° C. and 0.1 mm Hg. The distillation residue was chromatographed on silica gel with an eluent of ethyl acetate. The product, glycine, N-[(bis(tetrahydro-2H-pyran-2-yl methoxy)phosphinyl]methyl]-, ethyl ester was obtained as a viscous yellow oil in 57% yield (9.0 g) having the following analysis:

Calculated: C, 51.90; H, 8.20; N, 3.56; P 7.87; Found: C, 51.86; H, 8.34; N, 3.37; P, 7.48.

EXAMPLE 4

A reaction composition comprising 15.0 g (0.0402 mole) tri-[2-(1-pyrrolidinyl)ethyl]phosphite, 0.72 g (0.0402 mole) water, and 4.63 g (0.0134 mole) 1,3,5-tri(ethoxycarbonylmethyl)hexahydro-1,3,5-triazine was heated at about 25° C. for 1 hour and then at about 100° to about 110° C. for 3 hours. The reaction mixture was chromatographed on microcrystalline cellulose with an eluent of ethyl acetate. The product, glycine, N-[[(bis[2-(1-pyrrolidinyl)ethoxy]phosphinyl]methyl]-, ethyl ester was obtained as a viscous yellow oil in 41.3% yield (6.5 g) having the following analysis:

Calculated: C, 52.16; H, 8.75; N, 10.74; P, 7.91; Found: C, 52.62; H, 8.42; N, 10.85; P, 6.43.

EXAMPLE 5

A reaction composition comprising 15.0 g (0.0353 mole) butanoic acid, (3,3',3''-phosphinidyne tris(oxy)-tris-,triethyl ester, 0.64 g (0.0353 mole) water, and 4.08 g (0.0118 mole) 1,3,5-tri(ethoxycarbonylmethyl)hexahydro-1,3,5-triazine was heated at about 100° to about 110° C. for a time of 3 hours. An alcohol coproduct ethyl 3-hydroxybutanoate was removed by employing bulb to bulb distillation of the reaction mixture at ≦80° C. and 0.1 mm Hg. The phosphonate monoester product was obtained from a solution of ethyl acetate of the distillation residue upon standing at about 25° C. for 48 hours. The product butanoic acid, 3-[[[[(2-ethoxy-2-oxoethyl)amino]methyl]hydroxyphosphinyl]oxy]-, ethyl ester was obtained as a white solid in 8% yield (0.9 g) having a melting point of 116°–118° C. and having the following analysis:

Calculated: C, 42.44; H, 7.12; N, 4.50; P, 9.95; Found: C, 42.05; H, 7.11; N, 4.31; P, 9.98.

EXAMPLE 6

A reaction composition comprising 15.0 g (0.0315 mole) tri-(2,2,2-trichloroethyl)phosphite, 0.57 g (0.0315 mole) water, and 3.63 g (0.0105 mole) 1,3,5-tri(ethoxycarbonylmethyl)hexahydro-1,3,5-triazine was heated at about 100° to about 110° C. for a time of 3 hours. The reaction mixture was chromatographed on microcrystalline cellulose with an eluent of ethyl acetate. The product was precipitated from ethyl acetate eluent during 12 hours standing at 25° C. The product, glycine, N-[[(2,2,2-trichloroethoxy)hydroxyphosphinyl]methyl]-, ethyl ester, hydrate was obtained as a white solid in 14.7% yield (1.6 g) having a melting point of 143°–145° C. and having the following analysis:

Calculated: C, 24.26; H, 4.36; N, 4.04; P, 8.94; Found: C, 24.42; H, 3.48; N, 3.66; P, 7.87.

EXAMPLE 7

A reaction composition comprising 15.0 g (0.0315 mole) tri-(2,2,2-trichloroethyl)phosphite, 0.57 g (0.0315 mole) water, and 3.63 g (0.0105 mole) 1,3,5-tri(ethoxycarbonylmethyl)hexahydro-1,3,5-triazine was heated at about 100° to about 110° C. for a time of 3 hours. The reaction mixture was chromatographed on micro-crystalline cellulose with an eluent of ethyl acetate. Upon standing for 12 hours at about 25° C. a hydrated form of the product precipitated. Upon standing the ethyl acetate filtrate after an additional 12 hours at 25° C. deposited the present product which was collected and dried at 40° C. and 0.1 mmHg over $P_2O_5$. The product, glycine, N-[[hydroxy(2,2,2-trichloroethoxy)phosphinyl]methyl]-, ethyl ester was obtained as a white solid in 10.6% yield (1.1 g) having a melting point of 197°–199° C. and having the following analysis:

Calculated: C, 25.59; H, 3.99; N, 4.26; P, 9.43; Found: C, 25.85; H, 3.74; N, 4.44; P, 9.31.

If desired, a diester of formula (I) may be hydrolysized to a monoester of formula (I) by controlled hydrolysis. The temperature is in the range from about 15° to about 50° C. and is preferably from about 20° to about 30° C. The hydrolysis time is in the range from abou 10 to about 60 and preferably from about 20 to about 40 minutes.

EXAMPLE 8

This Example illustrates the production of a monosubstituted phosphonate from the corresponding disubstituted phosphonate derivative.

A reaction composition comprising 8.0 g (0.028 mole) of ethyl N[[bis 1-(1-methoxycarbonyl)ethoxy]phosphinyl]methylglycinate illustrative of a diester compound of formula (I) and 0.51 g (0.028 mole) water was agitated at about 25° C. for 30 minutes. The reaction mixture was chromatographed on a cation exchange column with water as eluent. The product, propanoic acid, 2-[[[[(2-ethoxy-2-oxoethyl)amino]methyl]hydroxyphosphinyl]oxy]-, methyl ester hydrate was isolated as the fourth component determined by a refractive index detector in 41.6% yield (3.30 g) having the following analysis and formula:

Calculated: C, 36.10; H, 6.67; N, 4.68; P, 10.34; Found: C, 36.18; H, 6.11; N, 4.56; P, 10.38.

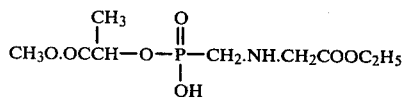

EXAMPLE 9

The post-emergent herbicidal activity of some of the various compounds of this invention was demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species were placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan except for the control pans is removed individually to a spraying chamber and sprayed by means of an atomizer operating at a positive air pressure of approximately 1.46 kg/cm² absolute. The atomizer contains 6 ml of a solution or suspension of the chemical. In that 6 ml. is an amount of a cyclohexanone emulsifying agent mixture to give a spray solution or suspension which contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded. In some instances, the two-week observations are omitted.

The post-emergent herbicidal activity index used in Tables I and II is as follows:

| Plant Response | Index |
|---|---|
| 0–24% control | 0 |
| 25–49% control | 1 |
| 50–74% control | 2 |
| 75–99% control | 3 |
| 100% control | 4 |

The plant species utilized in these tests are identified by letter in accordance with the following legend:

| | |
|---|---|
| A — Canada Thistle* | K — Barnyardgrass |
| B — Cocklebur | L — Soybean |
| C — Velvetleaf | M — Sugar Beet |
| D — Morningglory | N — Wheat |
| E — Lambsquarters | O — Rice |
| F — Smartweed | P — Sorghum |
| G — Yellow Nutsedge* | Q — Wild Buckwheat |
| H — Quackgrass* | R — Hemp Sesbania |
| I — Johnsongrass* | S — Panicum Spp |
| J — Downy Brome | T — Crabgrass |

*Established from vegetative propagules.

TABLE I

| Compound of Example No. | WAT | kg/h | A | B | C | D | E | F | G | H | I | J | K |
|---|---|---|---|---|---|---|---|---|---|---|---|---|---|
| 1 | 4 | 56.0 | 3 | 2 | 1 | 2 | 2 | 1 | 1 | 1 | 1 | 1 | 2 |
|   | 4 | 11.2 | 0 | 0 | 0 | 1 | 0 | 0 | 0 | 0 | 0 | 0 | 0 |
| 2 | 4 | 56.0 | 2 | 2 | 2 | 2 | 3 | 3 | 2 | 3 | 1 | 2 | 3 |
|   | 4 | 11.2 | 0 | 0 | 0 | 1 | 0 | 0 | 0 | 0 | 0 | 0 | 3 |
| 3 | 4 | 11.2 | 0 | 0 | 0 | 1 | 0 | 1 | 0 | 0 | — | 0 | 1 |
|   | 2 | 5.6 | 0 | 0 | 0 | 0 | 0 | 0 | 0 | 0 | 0 | 0 | 0 |
| 4 | 4 | 11.2 | 1 | 2 | 1 | 2 | 1 | 2 | 1 | 2 | 2 | 1 | 3 |
|   | 4 | 5.6 | 1 | 1 | 1 | 1 | 3 | 2 | 2 | 1 | 1 | 0 | 2 |
| 5 | 4 | 11.2 | 1 | 2 | 1 | 2 | 0 | 0 | 2 | 1 | 2 | 0 | 2 |
|   | 4 | 5.6 | 0 | 0 | 0 | 1 | 0 | 0 | 0 | 0 | 1 | 0 | 1 |
| 6 | 4 | 11.2 | 0 | 1 | 0 | 0 | 1 | 0 | 0 | 0 | 0 | 0 | 1 |
|   | 4 | 56.0 | 0 | 1 | 0 | 1 | 1 | 1 | 0 | 0 | 0 | 0 | 1 |
| 7 | 4 | 11.2 | 2 | 2 | 2 | 2 | 3 | 2 | 2 | 1 | 0 | 0 | 3 |
|   | 4 | 5.6 | 1 | 2 | 1 | 2 | 3 | 2 | 0 | 1 | 2 | 0 | 3 |
| 8** | 4 | 11.2 | 1 | 2 | 2 | 3 | 3 | 3 | 3 | 2 | 3 | 1 | 2 |
|   | 4 | 5.6 | 1 | 1 | 0 | 1 | 0 | 0 | 1 | 0 | 2 | 1 | 2 |

**Sprayed in 100 gallon per acre tetrahydrofuran immediately after formulation.

TABLE II

| Compound of Example No. | WAT | kg/h | L | M | N | O | P | B | Q | D | R | E | F | C | J | S | K | T |
|---|---|---|---|---|---|---|---|---|---|---|---|---|---|---|---|---|---|---|
| 2 | 4 | 5.6 | 0 | 0 | 1 | 0 | 1 | 0 | 2 | 1 | — | 0 | — | 1 | 0 | 3 | 2 | 2 |
|   | 2 | 1.12 | 0 | 0 | 0 | 0 | 0 | — | 0 | 0 | 2 | 1 | — | 0 | 0 | 0 | 1 | 1 |
| 4 | 4 | 5.6 | 2 | 1 | 2 | 2 | 2 | 3 | 1 | 2 | — | 3 | 2 | 2 | 2 | 4 | 3 | 4 |
|   | 4 | 1.12 | 0 | 0 | 0 | 0 | 0 | 0 | 0 | 1 | 1 | 1 | 1 | 1 | 0 | 1 | 1 | 2 |
| 7 | 4 | 5.6 | 3 | 3 | 4 | 4 | 3 | 3 | 3 | 2 | 3 | 3 | 3 | 2 | 3 | 4 | 3 | 4 |
|   | 4 | 1.12 | 2 | 2 | 2 | 3 | 2 | 2 | 2 | 2 | 2 | 2 | 2 | 1 | 3 | 4 | 3 | 3 |
|   | 4 | 0.28 | 2 | 2 | 3 | 3 | 2 | 2 | 2 | 2 | 2 | 1 | 1 | 3 | 1 | 3 | 3 | 3 |
|   | 2 | 0.06 | 0 | 0 | 0 | 0 | 0 | 0 | 0 | 0 | 0 | 0 | 0 | 0 | 0 | 0 | 0 | — |
|   | 2 | 0.01 | 0 | 0 | 0 | 0 | 0 | 0 | 0 | 0 | 0 | 0 | 0 | 0 | 0 | 0 | 0 | — |
| 8 | 4 | 5.6 | 1 | 0 | 1 | 2 | 2 | 2 | 0 | 2 | 3 | 1 | 1 | 0 | 0 | 2 | 3 | 3 |
|   | 2 | 1.12 | 1 | 0 | 0 | 0 | 0 | 0 | 0 | 1 | 0 | 0 | 0 | 0 | 0 | 0 | 1 | 2 |

— Plant species absent during test.

From the test results presented in Tables I and II, it can be seen that the post-emergent herbicidal activity of the compounds of this invention is, for the most part, general in nature. In certain specific instances, however, some selectivity is demonstrated. In this regard it should be recognized that each individual species selected for the above tests is a representative member of a recognized family of plant species.

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Preferably, the compositions of this invention contain from 5 to 75 parts by weight of at least one compound of this invention, together with the adjuvants. Where required, from about 0.1 to 2.0 parts by weight of the inert liquid extender can be replaced by a corrosion inhibitor such as ethanol mercaptan, sodium thiosulfate, dodecylmono or dimercaptan or anti-foaming agent such as a dimethylpolysiloxane, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid or organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent", it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

The following list gives some specific herbicidal compositions of this invention. It is to be realized that the solvents and surfactants are interchangeable in the composition.

| | | |
|---|---|---|
| 1. | Glycine, N—[[bis(2-furanylmethoxy)-phosphinyl]methyl]-, ethyl ester | 95 parts |
| | Methanol | 5 parts |
| 2. | Glycine, N—[[bis[(2,2-dimethyl-1,3-dioxolan-4-yl)methoxy]phosphinyl]-methoxy]-, ethyl ester | 5 parts |
| | Ethoxylated nonyl phenol | 5 parts |
| 3. | Glycine, N—[[bis(tetrahydro-2H—pyran-2-yl-methoxy)phosphinyl]-methyl]-, ethyl ester | 90 parts |
| | Isopropanol | 10 parts |
| 4. | Glycine, N—[[bis(2-furanylmethoxy)-phosphinyl]methyl]-, ethyl ester | 90 parts |
| | Ethoxylated octyl phenol | 10 parts |
| 5. | Glycine, N—[[bis[(2,2-dimethyl-1,3-dioxolan-4-yl)methoxy]phosphinyl]-methoxy]-, ethyl ester | 90 parts |
| | Chloroform | 5 parts |
| | Ethoxylated dinonyl phenol | 5 parts |
| 6. | Glycine, N—[[bis(tetrahydro-2H—pyran-2-yl-methoxy)phosphinyl]-methyl]-, ethyl ester | 75 parts |
| | α-butyrolactone | 25 parts |
| 7. | Glycine, N—[[bis(2-furanylmethoxy)- | 75 parts |

-continued

| | |
|---|---|
| phosphinyl]methyl]-, ethyl ester Ethoxylated oleyl alcohol | 25 parts |
| 8. Glycine, N—[[bis[(2,2-dimethyl-1,3-dioxolan-4-yl)methoxy]phosphinyl]methoxy]-, ethyl ester | 75 parts |
| Acetonitrile | 15 parts |
| Ethoxylated cocoamine | 10 parts |
| 9. Glycine, N—[[bis(tetrahydro-2H—pyran-2-yl-methoxy)phosphinyl]methyl]-, ethyl ester | 75 parts |
| 1,2-Dimethoxyethane | 20 parts |
| Ethoxylated tallow amine | 5 parts |
| 10. Glycine, N—[[bis(2-furanylmethoxy)phosphinyl]methyl]-, ethyl ester | 50 parts |
| Dimethylformamide | 50 parts |
| 11. Glycine, N—[[bis[(2,2-dimethyl-1,3-dioxolan-4-yl)methoxy]phosphinyl]methoxy]-, ethyl ester | 50 parts |
| Isopropyl dodecylbenzene sulfonate | 50 parts |
| 12. Glycine, N—[[bis(2-furanylmethoxy)phosphinyl]methyl]-, ethyl ester | 50 parts |
| Dimethylsulfoxide | 40 parts |
| Ethoxylated soybeanamine | 10 parts |
| 13. Glycine, N—[[bis-[2-(1-pyrrolidinyl)ethoxy]phosphinyl]methyl]-, ethyl ester | 50 parts |
| butyrolactone | 25 parts |
| Triethanolamine dodecylbenzene sulfonate | 25 parts |
| 14. Glycine, N—[[bis-[2-(1-pyrrolidinyl)ethoxy]phosphinyl]methyl]-, ethyl ester | 50 parts |
| 1,1,1-Trichloroethane | 42 parts |
| Ethoxylated nonyl phenol | 8 parts |
| 15. Glycine, N—[[bis-[2-(1-pyrrolidinyl)ethoxy]phosphinyl]methyl]-, ethyl ester | 25 parts |
| Chloroform | 75 parts |
| 16. Glycine, N—[[bis-[2-(1-pyrrolidinyl)ethoxy]phosphinyl]methyl]-, ethyl ester | 25 parts |
| Chloroform | 70 parts |
| Ethoxylated tallow amine | 5 parts |
| 17. Glycine, N—[[bis(2-furanylmethoxy)phosphinyl]methyl]-, ethyl ester | 25 parts |
| 1,1,1-Trichloroethane | 74 parts |
| Ethoxylated oleyl alcohol | 1 part |
| 18. Glycine, N—[[bis[(2,2-dimethyl-1,3-dioxolan-4-yl)methoxy]phosphinyl]methoxy]-, ethyl ester | 10 parts |
| Chloroform | 90 parts |
| 19. Glycine, N—[[bis(tetrahydro-2H—pyran-2-yl-methoxy)phosphinyl]methyl]-, ethyl ester | 10 parts |
| Methanol | 80 parts |
| Polyoxypropylene - polyoxyethylene block copolymer | 10 parts |
| 20. Glycine, N—[[bis(2-furanylmethoxy)phosphinyl]methyl]-, ethyl ester | 10 parts |
| Ethanol | 88 parts |
| Polyoxyethylene (20) sorbitan-monolaurate | 2 parts |
| 21. Glycine, N—[[bis[(2,2-dimethyl-1,3-dioxolan-4-yl)methoxy]phosphinyl]methoxy]-, ethyl ester | 10 parts |
| Isopropanol | 72 parts |
| Polyoxyethylene sorbitan-monooleate | 18 parts |
| 22. Glycine, N—[[bis-[2-(1-pyrrolidinyl)ethoxy]phosphinyl]methyl]-, ethyl ester | 5 parts |
| Acetonitrile | 90 parts |
| Ethoxylated tallow amine | 5 parts |
| 23. Glycine, N—[[bis(tetrahydro-2H—pyran-2-yl-methoxy)phosphinyl]methyl]-, ethyl ester | 5 parts |
| Isopropanol | 80 parts |
| Ethoxylated cocoamine | 15 parts |

The ingredients for examples 24–43 are blended and ground to approximately 20–40 mesh to give the final formulation. Other wetting agents and water-soluble fillers may be employed if desired. In the list following hereafter E = Butanoic acid, 3-[[[[(2-ethoxy-2-oxoethyl)amino]methyl]hydroxyphosphinyl]oxy]-, ethyl ester F = Glycine, N-[[(2,2,2-trichloroethoxy)hydroxyphosphinyl]methyl]-, ethyl ester, hydrate G = Glycine, N-[[hydroxy(2,2,2-trichloroethoxy)phosphinyl]methyl]-, ethyl ester H = Propanoic acid, 2-[[[[(2-ethoxy-2-oxoethyl)amino]methyl]hydroxyphosphinyl]oxy]-, methyl ester.

| | Formulation No. | | | | |
|---|---|---|---|---|---|
| Composition: | 24 | 25 | 26 | 27 | 28 |
| E | 80.00 | 90.00 | 95.00 | 98.50 | 100 |
| Aerosol OTB | 2.00 | 2.00 | 2.00 | 1.50 | 0 |
| Urea | 18.00 | 8.00 | 3.00 | 0 | 0 |

| Composition: | 29 | 30 | 31 |
|---|---|---|---|
| F | 80.00 | 90.00 | 95.00 |
| Sodium lauryl-sulfate | 2.00 | 2.00 | 1.50 |
| Urea | 18.00 | 8.00 | 3.50 |

| Composition: | 32 | 33 | 34 | 35 | 36 | 37 | 38 |
|---|---|---|---|---|---|---|---|
| G | 10.00 | 25.00 | 45.00 | 65.00 | 80.00 | 90.00 | 99.00 |
| nonyl phenol-poly oxyethylene ether | 1.00 | 2.00 | 2.00 | 3.00 | 4.00 | 5.00 | 1.00 |
| monoammonium-phosphate | 89.00 | 73.00 | 53.00 | 32.00 | — | — | — |
| sucrose | — | — | — | — | 16.00 | 5.00 | — |

| Composition: | 39 | 40 | 41 | 42 | 43 |
|---|---|---|---|---|---|
| H | 80.00 | 90.00 | 95.00 | 98.50 | 100 |
| Aerosol OTB | 2.00 | 2.00 | 2.00 | 1.50 | 0 |
| Urea | 18.00 | 8.00 | 3.00 | 0 | 0 |

When operating in accordance with the present invention, effective amounts of the compounds or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.112 to about 56.0 or more kilograms per hectare. In pre-emergent treatments, the rate of application can be from about 0.56 to about 22.4 or more kilograms per hectare. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

There are several methods for applying liquid compositions of this invention to emerged plants. Such methods include the use of wiper systems whereby the plant to be treated is contacted with an absorbent material containing the particular liquid composition, a portion of which is thereby released onto the plant upon contact therewith. Such wiper systems typically comprise a reservoir of the liquid composition into which a portion of the absorbent material is placed and is fed therethrough. Generally, substances employable as absorbent material include substances of any shape or form capable of absorbing the liquid composition and releasing a portion of the same upon contact with the plant. Typical absorbent materials include felt, foam rubber, cellulose, nylon, sponges, hemp, cotton, burlap, polyester over acrylic, combinations thereof and the like. Forms of absorbent material include rope, twine, string, cloths, carpets, combinations thereof and the like. These forms may be assembled in any manner desired including a pipe rope wick, a wedge rock wick, a multi-rope wick and the like.

In another application method, liquid compositions may be selectively applied to weeds by the use of recirculating sprayer systems wherein the recirculating spray unit is mounted on a tractor or high clearance mobile equipment and the spray is directed horizontally onto the weeds growing over a crop. Spray not intercepted by the weeds is collected in a recovery chamber before contacting the crop and is reused. Roller applications may also be employed to apply liquid compositions to weeds growing over a crop.

In yet another application method, shielded applicators may be employed to direct the liquid composition in the form of a spray onto the weeds while effectively shielding the crops from the spray.

These and other application methods for selectively applying liquid compositions to weeds are discussed in detail in Innovative Methods of Post-Emergence Weed Contol, McWhorter C. G, Southern Weed Science Society, 33rd Annual Meeting Proceedings, Jan. 15-17, 1980; Auburn University Printing Service, Auburn, Ala. U.S.A., the teachings of which are incorporated herein by reference in their entirety.

Another method of applying liquid compositions of this invention to plants includes controlled droplet application which is also known as the ultra low-volume chemical application. Controlled droplet application involves the production of uniform or nearly uniform spray drops of a predetermined size and the conveyance of these drops with negligible evaporation to a spray target. In particular, this method comprises feeding spray solutions to a rotary atomizer comprising a small disk with serrated edges that disperses liquid into droplets as the disk spins. Different droplet sizes are produced by changing solution flow rates to the spinning disk or changing the speed of rotation of the disk.

The aforementioned and other methods for applying liquid compositions to plants are discussed in detail in "Rope Wick Applicator—Tool With A Future", Dale, James E., pp. 3-4, "The Recirculating Sprayer and Roundup ® Herbicide", Derting, Claude W., pp. 5-7, and "C.D.A. Herbicide Application", McGarvey, Frank X., *Weeds Today,* Volume 11, Number 2, pp. 8-9, Late Spring, 1980, 309 W. Clark St., Champaign, Ill., the teachings of which are incorporated herein by reference in their entirety.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. Alkylphosphonate esters of N-phosphonomethylglycinate of the formula

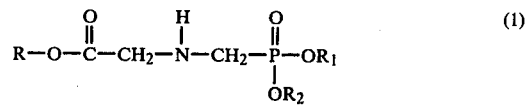

wherein R is lower alkyl; $R_1$ is a

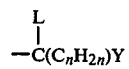

group wherein n is an integer of from 0 to 4, L is hydrogen or lower alkyl and Y is selected from the group consisting of trihalomethyl, alkoxycarbonyl, furanyl, pyrrolidinyl, pyranyl group and a

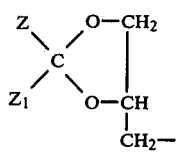

group wherein Z and $Z_1$ are independently lower alkyl, and $R_2$ is hydrogen or a group represented by $R_1$ provided that when Y is alkoxycarbonyl, $R_2$ is hydrogen.

2. A compound of claim 1 wherein R is ethyl.

3. A compound of claim 1, wherein $R_2$ is the same group as represented by $R_1$ and R is ethyl.

4. A compound of claim 1 wherein $R_1$ is —$(C_nH_{2n})$—Y n is an integer from 1 to 4, and R is ethyl.

5. A compound of claim 4 wherein Y is furanyl.

6. A compound of claim 4 wherein Y is dioxolanyl.

7. A compound of claim 4 wherein Y is pyranyl.

8. A compound of claim 3, wherein $R_1$ is —$(C_2H_4)$—Y, wherein Y is pyrrolidinyl.

9. A compound of claim 2, wherein $R_2$ is hydrogen.

10. A compound of claim 9, wherein $R_1$ is —$(C_nH_{2n})$—Y.

11. A compound of claim 10, wherein n is 2.

12. A compound of claim 11, wherein Y is ethoxycarbonyl.

13. A compound of claim 11, wherein Y is trichloromethyl.

14. A compound of claim 10, wherein n is 1 and Y is trichloromethyl.

15. A compound of claim 10, wherein n is 4 and Y is ethoxycarbonyl.

16. A herbicidal composition comprising a herbicidally effective amount of a compound of claim 1, together with an inert diluent.

17. A herbicidal composition comprising a herbicidally effective amount of a compound of claim 2, together with an inert diluent.

18. A herbicidal composition comprising a herbicidally effective amount of a compound of claim 3, together with an inert diluent.

19. A herbicidal composition comprising a herbicidally effective amount of a compound of claim 4, together with an inert diluent.

20. A herbicidal composition comprising a herbicidally effective amount of a compound of claim 5, together with an inert diluent.

21. A herbicidal method which comprises contacting a plant with a herbicidally effective amount of a compound of claim 1.

22. A herbicidal method which comprises contacting a plant with a herbicidally effective amount of a compound of claim 2.

23. A herbicidal method which comprises contacting a plant with a herbicidally effective amount of a compound of claim 3.

24. A herbicidal method which comprises contacting a plant with a herbicidally effective amount of a compound of claim 4.

25. A herbicidal method which comprises contacting a plant with a herbicidally effective amount of a compound of claim 5.

* * * * *